United States Patent
Hailmann et al.

(10) Patent No.: US 9,603,744 B2
(45) Date of Patent: Mar. 28, 2017

(54) ADAPTABLE PATIENT INTERFACE

(71) Applicant: Technolas Perfect Vision GmbH, Munich (DE)

(72) Inventors: Markus Hailmann, München (DE); Florian Dambacher, Haag (DE); Frieder Loesel, Mannheim (DE); Gwillem Mosedale, München (DE)

(73) Assignee: Technolas Perfect Vision GmbH, Munich (DE)

( * ) Notice: Subject to any disclaimer, the term of this patent is extended or adjusted under 35 U.S.C. 154(b) by 691 days.

(21) Appl. No.: 13/796,047

(22) Filed: Mar. 12, 2013

(65) Prior Publication Data

US 2014/0135750 A1 May 15, 2014

Related U.S. Application Data

(60) Provisional application No. 61/724,692, filed on Nov. 9, 2012.

(51) Int. Cl.
 *A61B 1/32* (2006.01)
 *A61F 9/009* (2006.01)

(52) U.S. Cl.
 CPC .................................. *A61F 9/009* (2013.01)

(58) Field of Classification Search
 CPC ...... A61F 9/007; A61F 9/00736; A61F 9/008; A61F 9/009
 USPC ............... 606/4–6; 427/2.24; 600/236
 See application file for complete search history.

(56) References Cited

U.S. PATENT DOCUMENTS

| | | |
|---|---|---|
| 4,848,340 A | 7/1989 | Bille et al. |
| 4,856,513 A | 8/1989 | Muller |
| 4,905,711 A | 3/1990 | Bennett et al. |
| 4,907,872 A | 3/1990 | Schirmer et al. |
| 4,994,058 A | 2/1991 | Raven et al. |
| 5,108,412 A | 4/1992 | Krumeich et al. |
| 5,336,215 A | 8/1994 | Hsueh et al. |
| 5,549,632 A | 8/1996 | Lai |
| 5,779,696 A | 7/1998 | Berry et al. |

(Continued)

FOREIGN PATENT DOCUMENTS

| | | | |
|---|---|---|---|
| CA | 2735264 A1 | 4/2010 | |
| EP | 1844744 A1 | 10/2007 | |

(Continued)

*Primary Examiner* — Ellen C Hammond
*Assistant Examiner* — Christina Negrellirodrigue
(74) *Attorney, Agent, or Firm* — Nydegger & Associates

(57) ABSTRACT

Systems and methods are described for stabilizing an eye for an ocular laser procedure while minimizing corneal distortions which can adversely affect a surgical laser beam. For the systems, a patient interface includes a contact element for stabilizing the eye and establishing a conformal interface with the anterior surface of the cornea. More specifically, devices are disclosed which overlay both a central corneal region and a peripheral corneal region. In some embodiments, a first material is used in the contact element to overlay the central corneal region and a second material is used in the contact element to overlay the peripheral corneal region. Typically, the first and second materials differ in terms of hardness and deformability. In another embodiment disclosed herein, a contact element having a viscoelastic material for stabilizing an eye for a laser procedure is described.

15 Claims, 6 Drawing Sheets

(56) References Cited

U.S. PATENT DOCUMENTS

| | | |
|---|---|---|
| 5,865,830 A | 2/1999 | Parel et al. |
| 6,143,011 A | 11/2000 | Hood et al. |
| 6,373,571 B1 | 4/2002 | Juhasz et al. |
| 6,467,906 B1 | 10/2002 | Alpins |
| 6,730,074 B2 | 5/2004 | Bille et al. |
| 6,751,033 B2 | 6/2004 | Goldstein et al. |
| 6,863,667 B2 | 3/2005 | Webb et al. |
| 6,966,905 B2 | 11/2005 | Bille |
| 7,018,376 B2 | 3/2006 | Webb et al. |
| 7,125,119 B2 | 10/2006 | Farberov |
| 7,371,230 B2 | 5/2008 | Webb et al. |
| 7,390,089 B2 | 6/2008 | Loesel et al. |
| 7,402,159 B2 | 7/2008 | Loesel et al. |
| 7,611,507 B2 | 11/2009 | Raksi et al. |
| 7,692,865 B2 | 4/2010 | Muehlhoff et al. |
| 7,836,892 B2 | 11/2010 | Dick et al. |
| 7,955,324 B2 | 6/2011 | Melcher et al. |
| 7,976,155 B2 | 7/2011 | Muehlhoff et al. |
| 8,496,583 B1* | 7/2013 | Reynard ............ A61B 17/0231 600/235 |
| 2007/0237620 A1 | 10/2007 | Muehlhoff et al. |
| 2008/0183159 A1 | 7/2008 | Preuss et al. |
| 2008/0228176 A1 | 9/2008 | Triebel et al. |
| 2008/0234707 A1 | 9/2008 | Muehlhoff |
| 2009/0069794 A1 | 3/2009 | Kurtz |
| 2009/0163773 A1* | 6/2009 | Lin .................... A61F 9/00727 600/236 |
| 2010/0022994 A1 | 1/2010 | Frey et al. |
| 2010/0210996 A1* | 8/2010 | Peyman ................ A61F 7/007 604/20 |
| 2010/0274228 A1 | 10/2010 | Mrochen et al. |
| 2011/0022035 A1 | 1/2011 | Porter et al. |
| 2011/0040293 A1 | 2/2011 | Bor |
| 2011/0102810 A1 | 5/2011 | Bischoff et al. |
| 2011/0166557 A1 | 7/2011 | Naranjo-Tackman et al. |
| 2011/0238045 A1 | 9/2011 | Dick et al. |
| 2011/0304819 A1 | 12/2011 | Juhasz et al. |
| 2011/0319873 A1* | 12/2011 | Raksi .................... A61F 9/009 606/1 |
| 2012/0016349 A1 | 1/2012 | Brownell |
| 2012/0078241 A1 | 3/2012 | Gooding et al. |
| 2012/0172854 A1 | 7/2012 | Raymond et al. |

FOREIGN PATENT DOCUMENTS

| | | |
|---|---|---|
| WO | 9515134 | 6/1995 |
| WO | 2006002392 A2 | 1/2006 |
| WO | 2007127257 A3 | 11/2007 |
| WO | 2009003609 A2 | 3/2009 |
| WO | 2009073502 A2 | 6/2009 |
| WO | 2012041347 A1 | 4/2012 |

* cited by examiner

ADAPTABLE PATIENT INTERFACE

This application claims the benefit of U.S. Provisional Patent Application Ser. No. 61/724,692, titled ADAPTABLE PATIENT INTERFACE, filed Nov. 9, 2012. The entire contents of Application Ser. No. 61/724,692 are hereby incorporated by reference herein.

FIELD OF THE INVENTION

The present invention pertains generally to systems and methods for performing ophthalmic surgery. More particularly, the present invention pertains to systems and methods for stabilizing an eye during ophthalmic surgery. The present invention is particularly, but not exclusively, useful as a system and method that stabilizes the eye with a contact element while causing minimal changes in refractive properties of the eye during ophthalmic surgery.

BACKGROUND OF THE INVENTION

Surgical lasers are now commonly used in a variety of ophthalmic surgical procedures, including the treatment of ocular diseases and the correction of optical deficiencies. In these procedures, the surgical laser is often chosen as the tool of choice because of the ability of the laser to be accurately focused with great precision. In addition, the ability of the laser to be guided to designated locations within the eye, with precision and reliability, has enabled ophthalmic procedures to be performed throughout the eye.

Anatomical characteristics of the eye, however, can undermine the effectiveness of any laser procedure. In particular, this is so for ophthalmic laser surgery that is to be performed on tissue behind (i.e. posterior) the cornea. Specifically, the beam of a laser can be significantly degraded by wrinkles that may be induced predominantly on the posterior surface of the cornea of an eye, when the eye is being stabilized by a contact element. The effect of these wrinkles becomes most acute when the laser beam is used for procedures on tissues in the deeper regions of the eye beyond the cornea, such as the lens or the retina.

Typically, when an eye stabilizing device is used, it is placed against the anterior surface of the eye and is pressed in a posterior direction. As a consequence, tissue in the eye may be squeezed in a manner that will cause wrinkles to be created primarily on the posterior surface of the cornea of the eye. These wrinkles can then cause an undesirable refraction, dispersion and degradation of the laser beam, as well as other adverse optical effects, as it passes through the cornea. An additional drawback caused by dispersion of the laser beam is the possibility of unintentionally damaging non-targeted tissue.

Typically, during an ocular laser procedure, an interface device is employed to dock a laser system with a patient's cornea. Once docked, the anterior corneal surface is fixed in four dimensions (i.e. x, y, z and over time t) relative to the laser system. As indicated above, prevention of folds on the posterior corneal surface can be important for procedures extending posteriorly to the cornea.

The shape of the anterior surface of the cornea and the variation of corneal shape and size across the patient population can complicate the selection and application of a suitable contact surface. In this regard, at the macroscopic level, the anterior surface of the cornea generally includes two regions. These include a central region with a relatively steep curvature that is surrounded by a peripheral region have a flatter curvature. The actual size and curvature of the regions varies from patient to patient.

Currently used patient interfaces typically have either non-deformable solid or liquid contact surfaces. Solid interfaces have typically been used in corneal procedures while liquid interfaces have more recently been developed for use in cataract surgery. Typically, for these procedures, a patient interface that establishes contact with both the central and peripheral regions of the cornea is used. Recall that these regions differ in curvature. Because of this curvature difference, when a solid interface is used to contact both the central and peripheral regions of the cornea, a substantial flattening of the central region can occur, resulting in corneal deformation and, in some cases, wrinkle formation on the posterior corneal surface. Specifically, current all-purpose solid patient interfaces designed to accommodate a wide patient population with its inherent anatomical variations typically include a one-size-fits-all curvature of 32 diopters.

In addition to stabilizing and aligning the cornea relative to the laser system, it is also desirable to stabilize the eye by reducing ocular movements induced by the patient's heartbeat. In particular, a number of corneal applications such as LASIK flaps, intrastromal relaxing incisions, and others are sensitive to these heartbeat induced ocular movements. In some cases, it may be desirable to include one or more direct contact areas between a solid, non-deformable part of a patient interface substantially over (or in the vicinity of) a diameter which prevents movement induced by heartbeat in the areas of the cornea targeted by these procedures. In this regard, corneal flap incisions that are performed as part of LASIK surgery rarely have diameters larger than 9.5 mm. Meanwhile, cataract incisions such as Limbal Relaxing Incisions (LRI) may be performed more peripherally than the incisions cited above, and are typically less sensitive to heartbeat induced ocular movements.

In light of the above, it is an object of the present invention to provide a patient interface that can be used on patients within a patient population having differing corneal shapes and sizes. It is another object of the present invention to provide systems and methods for stabilizing a patient's eye for an ophthalmic laser treatment while minimizing cornea wrinkles in the cornea area where the treatment laser passes. It is yet another object of the present invention to provide systems and methods for stabilizing a patient's eye that reduces the adverse effects of heartbeat induced ocular movements. Yet another object of the present invention is to provide an adaptable patient interface and corresponding methods of use which are easy to use, relatively simple to implement, and comparatively cost effective.

SUMMARY OF THE INVENTION

In accordance with the present invention, devices and methods are provided for stabilizing an eye for an ocular laser procedure. More specifically, devices are described for physically restraining an eye to reduce or eliminate eye movements including heartbeat induced ocular movements. For the devices disclosed herein, stabilization can be achieved while minimizing corneal distortions which can adversely affect a surgical laser beam. For example, corneal distortions due to excessive pressures or misalignments during stabilization can cause folds (i.e. wrinkles) to develop on the posterior surface of the cornea. These folds can affect laser beam quality and are of particular concern for procedures that require passing a laser beam through the cornea.

With the above in mind, the present invention is directed to a patient interface having a contact element for stabilizing the eye and establishing a conformal interface with the anterior surface of the cornea. More specifically, devices are disclosed which overlay both a central corneal region, which typically has a relatively small radius of curvature, (or, since the cornea is normally aspheric, a range of relatively small radii of curvature) and a peripheral corneal region which typically has a relatively large radius of curvature, i.e. flatter curvature (or, since the cornea is normally aspheric, a range of relatively large radii of curvature).

More particularly, the devices of the present invention include a contiguous inner surface which overlays both the central corneal region and a peripheral corneal region and establishes a conformal interface with both regions. This allows a surgical or diagnostic laser beam to be directed into or through the central corneal region, a peripheral corneal region, or both.

In more structural detail, in the hybrid embodiments described herein, the contact element includes a substantially circular, disk-shaped central portion that defines an axis and a periphery. For the central portion, the periphery is positioned in a plane that is perpendicular to the axis and is located at a radial distance "$r_1$" from the axis. Moreover, the central portion is formed with a contact surface having a radius of curvature "$R_1$" when the central portion is in contact with the eye and is made of a laser transparent material having a hardness "$h_1$".

For these hybrid embodiments, the contact element also includes an annular-shaped peripheral portion that extends from the periphery of the central portion to establish the peripheral portion as an extension of the central portion beyond the distance "$r_1$" from the axis. Geometrically, the peripheral portion has an inner radius equal to "$r_1$", an outer radius of "$r_2$" and is formed with a contact surface having a nominal radius of curvature "$R_2$" when the peripheral portion is in contact with the eye. In addition, the peripheral portion is made of a transparent material having a hardness "$h_2$", wherein "$h_1 \neq h_2$" and "$R_1 < R_2$". In some cases, the central portion may have a more than one radii of curvature within a first radius of curvature range and the peripheral portion may have a more than one radii of curvature within a second radius of curvature range, with each radii of curvature in the first range being less that each radii of curvature in the second range, resulting in an aspheric surface.

As implied above, the contact element is formed with an inner surface having a selected curvature. Typically, this curvature is about 35-45 diopters. Moreover, for the hybrid embodiments, the contact element can include two distinct materials which together form the inner surface of the contact element. The first material is selected to be as hard or harder than the cornea. Thus, when the first material is pressed against the cornea, the first material is stabilizing the cornea. Typically, the first material is a solid, rigid material. Examples of the first material include glass, thermoplastics (e.g. PMMA), etc.

On the other hand, the second material is selected to be softer than the cornea and when pressed against the cornea, the cornea will deform less than the second material. Examples of the second material include a liquid, a gel, a viscoelastic, a liquid crystal, an elastic file, a membrane, a cream, an artificial tear, an elastic material, and a viscous material, and deformable solids such as silicone, acrylate, PVC, polymacon, methafilcon, etafilcon, etc.

For the above described device, the second material is also softer than the first material. The consequence of this is that the second material deforms more than the first material at the inner surface during an application of the contact element with the eye. In some implementations, the first and second materials have comparable refractive indexes. For example, in some embodiments, the first material has a refractive index, "$n_1$", and the second material has a refractive index, "$n_2$", and "$n_1$" is within about +/−6% of "$n_2$" (for example, for PMMA, n=1,491; for Polymacon n=1,43 and for Etafilcon n=1,40). In a first hybrid embodiment of the device, the contact element includes a central portion and a peripheral portion. Together, the portions form an inner surface which is contiguous between the portions. For this embodiment, the central portion is made of a material that is harder than the cornea (first material) and the peripheral portion is made of a material that is softer than the cornea (second material). The relatively hard central portion stabilizes the eye and prevents eye movements which could interfere with an ocular laser procedure. For this embodiment, the inner surface of the central portion can have a relatively large curvature of about 35-45 diopters. A consequence of this large central portion curvature is that the contact element does not substantially flatten the central corneal region when positioned on the cornea. On the other hand, the softer peripheral portion of the contact element can deform when positioned against the flatter peripheral corneal region.

Alternatively, the central portion may have the same curvature as a single material, one-size-fits-all interface, while the softer peripheral portion has a steeper (aspheric) curvature. This may deflect much of the pressure that is normally predominantly applied across the central region during docking from the center to the peripheral corneal region, causing less deformation (centrally and/or overall) while still maintaining good central contact.

Functionally, this arrangement allows a contact element having a higher central portion curvature (35-45 diopters) than would be allowable for a device having a single rigid material. Specifically, single material devices (i.e. where the single material is rigid) which overlay both a central corneal region and a flatter peripheral corneal region, including so-called one-size-fits-all patient interfaces, are generally limited to curvatures less than about 35 diopters. For the single material device, a flatter inner surface curvature is required to ensure that the device conforms to the cornea at the cornea's flatter peripheral region and to a wide variety of different curvatures within the patient population. However, the central region must be severely distorted to conform to the flatter curvature of the single material device. This distortion, in turn, can result in undesirable folds on the cornea's posterior surface. On the other hand, because of its larger central curvature and soft periphery, the device of the present invention can overlay and establish a conforming interface with both the central and peripheral corneal regions without substantial corneal distortion.

As indicated above, in one hybrid embodiment, the second material of the contact element can be a liquid. For this embodiment, the contact element includes a rigid central portion that is sized and shaped for direct contact with the cornea and typically has a central surface portion curvature of about 35 diopters. More specifically, the central portion can be disk-shaped defining an axis and a periphery located at a radial distance "$r_1$" and radius of curvature "$R_1$", as described above. In greater detail, the central portion is sized and shaped to establish a gap between the periphery of the central portion and the cornea. The annular-shaped peripheral portion is a liquid located in the gap and held between the central portion and the eye by capillary forces (i.e. surface tension forces). For this embodiment, the liquid peripheral portion has an inner radius less than "$r_1$" and establishes a radius of curvature "$R_2$" on the eye, with "$R_1 < R_2$". For example, this liquid may be a meniscus of liquid and may be the liquid routinely used by clinical staff to flush the cornea prior to surgery. For this embodiment, the hydrophilic properties of the first material can be considered during selection of the first material as these properties will have an effect on the formation of a meniscus.

In another hybrid embodiment, the contact element includes a central portion and a peripheral portion, which, together form an inner surface which is contiguous between portions. For this embodiment, the peripheral portion is made of the first material that is harder than the cornea and the central portion is made of the second material that is softer than the cornea. Typically, the central portion has an inner surface curvature of about 32-38 diopters. In this embodiment, the relatively hard peripheral portion stabilizes the eye while the relatively soft central portion deforms when positioned against the central corneal region without causing substantial corneal flattening. Since the central portion deforms, the central portion can have a curvature that is tighter than the range of individual corneal curvatures normally allowed in the patient population when using a single material contact interface.

For the embodiments described above, the portion of the device that includes the first material (i.e. the material that is harder than the cornea) substantially stabilizes the eye to reduce the effects of heartbeat induced ocular movements. More specifically, the effects of heartbeat induced ocular movements are reduced to a level suitable for ocular laser procedures such as an intrastromal relaxing incision procedure, a cataract incision (such as LRI) or a LASIK corneal flap/LASIK ablation.

In another embodiment, a device for stabilizing an eye for a laser procedure can include a contact element having a viscoelastic material. Specifically, a viscoelastic material may be used that is deformable in response to stresses applied over relatively long time periods and rigid in response to stresses applied over relatively short time periods. With this structure, the contact element can be slowly pressed onto the cornea allowing the viscoelastic material to deform. This allows the contact element to mold onto the cornea until the contact element conforms with the cornea's anterior surface. Additionally, with this structure, the contact element is able to stabilize the eye against heartbeat induced ocular movements. This is because these movements apply stresses over relatively short time periods in which the viscoelastic material remains substantially rigid and does not deform. For example, the viscoelastic material can be a viscous liquid or a gel.

The viscoelastic material could also be used as part of a hybrid (e.g. two materials) contact element, similar to the two material contact elements described above. For example, a device for stabilizing an eye for a laser procedure can include a contact element having central portion made of a viscoelastic material (as described above) and a peripheral portion made of a material that is harder than the cornea (as described above). Alternatively, a device for stabilizing an eye for a laser procedure can include a contact element having central portion made of a viscoelastic material (as described above) and a peripheral portion made of a material that is softer than the cornea (as described above). In another embodiment, a device for stabilizing an eye for a laser procedure can include a contact element having central portion made of a material that is harder than the cornea (as described above) and a peripheral portion made of a viscoelastic material (as described above). In yet another embodiment, a device for stabilizing an eye for a laser procedure can include a contact element having central portion made of a material that is softer than the cornea (as described above) and a peripheral portion made of a viscoelastic material (as described above).

In another embodiment, a device for stabilizing an eye for a laser procedure can include a contact element having a hardness that varies gradually across the surface of the contact element. For example, the hardness can vary gradually from hard in the center to soft at the periphery. To manufacture this gradual variation in hardness, 3D printing or any other suitable technique known in the pertinent art may be used.

The devices described herein for stabilizing an eye for an ocular laser procedure can also include a detector for real-time adjustment of alignment and/or docking pressure between the contact element and the eye. For example, the detector can include a pressure sensor, an imaging system, or both, to monitor an interaction between the contact element and the cornea. The purpose of the detector and associated control system is to adjust the alignment and docking pressure such that an optimal engagement of the cornea by the contact element is achieved and maintained. When optimized, the device prevents movements that are large enough to disrupt a surgical procedure while avoiding excessive stabilization forces that can distort the cornea and lead to unwanted degradations in laser beam quality. A suitable detector and associated control subsystem is disclosed and claimed in co-owned U.S. patent application Ser. No. 13/423,919, titled "APPARATUS AND METHOD FOR CONTROL OF REFRACTIVE INDEX CHANGES IN A MATERIAL" to Jochen Kandulla, filed Mar. 19, 2012, the entire contents of which are hereby incorporated by reference herein.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

BRIEF DESCRIPTION OF THE EMBODIMENTS

Figure 1:
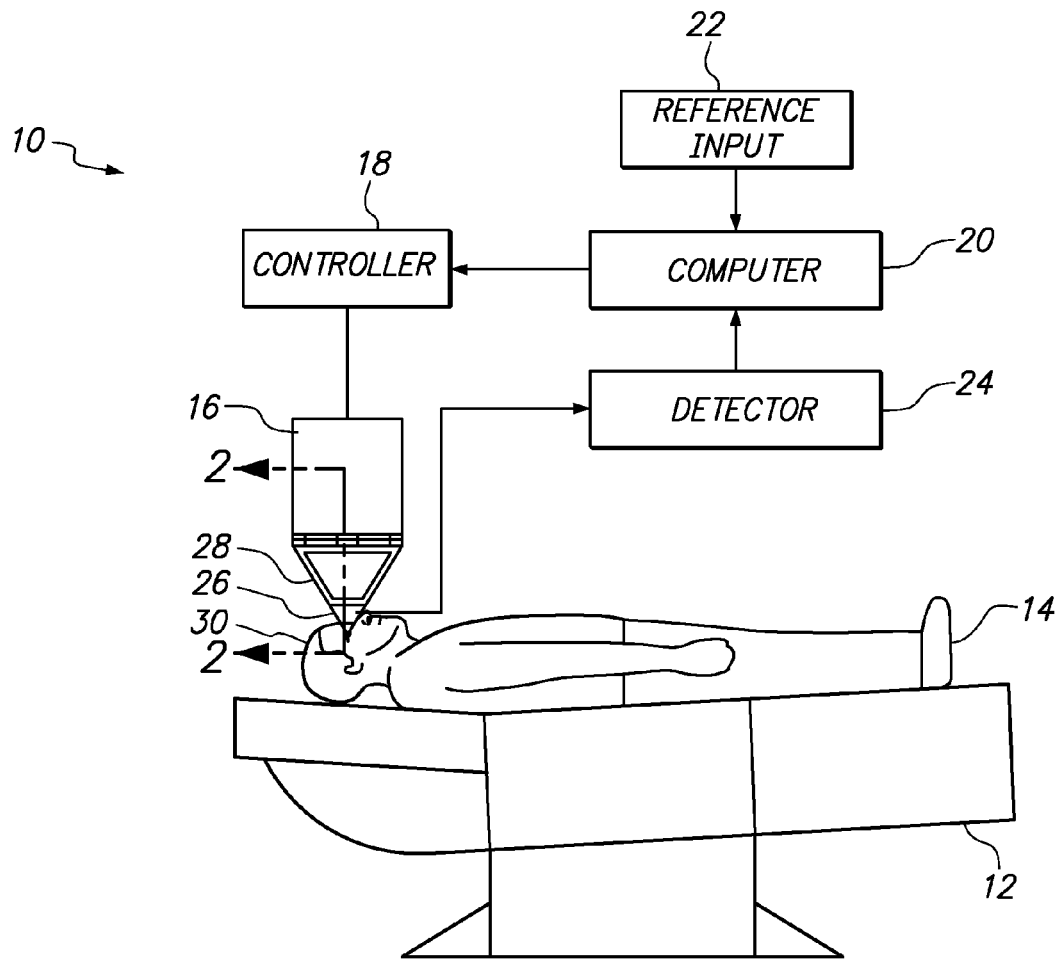
FIG. 1 is a schematic view of the components of a system of the present invention shown in operation with a patient.

Referring initially to FIG. 1, a system for performing an ophthalmic laser surgical procedure is shown and is generally designated 10. As shown, the system 10 can include a table 12 for supporting a patient 14 during the procedure. The system 10 can also include a laser unit 16 for generating a surgical laser beam that can be focused to treat subsurface ocular tissue as part of the procedure. Further, FIG. 1 shows that the system 10 can include a controller 18 for operating the laser unit 16, and a computer 20 that processes computer readable instructions for an operation of the controller 18.

FIG. 1 also indicates that the computer 20 can receive inputs from a reference input 22 and a detector 24. For some embodiments described herein, the detector 24 can provide information to the computer 20 that pertains to the interactive relationship between a contact element 26 and the patient 14. In particular, this interactive relationship can be monitored as the contact element 26 is moved by a placement device 28 into contact with an eye 30 of the patient 14. When used, the interactive relationship between the contact element 26 and the eye 30 can be monitored to ensure that the eye 30 is stabilized during an ophthalmic laser procedure without causing unwanted distortions of the eye 30. Further details regarding a system for real-time adjustment of alignment and/or docking pressure between the contact element 26 and the eye 30 can be found in co-owned, U.S. patent application Ser. No. 13/423,919, titled "APPARATUS AND METHOD FOR CONTROL OF REFRACTIVE INDEX CHANGES IN A MATERIAL" to Jochen Kandulla.

Figure 2:
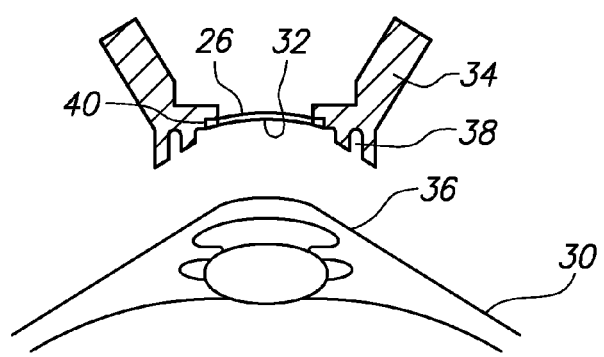
FIG. 2 shows a cross-sectional view as seen along line 2-2 in FIG. 1 showing an embodiment of a contact element in accordance with the present invention positioned over a patient's eye.

FIG. 2 shows a sectional view as seen along line 2-2 in FIG. 1. As shown, a contact element 26 having an inner surface 32 is held by an applicator 34 and can be applied to the cornea 36 of an eye 30. Once applied, the contact element 26 can be held in place by applying suction to a vacuum channel 38 formed in the applicator 34. FIG. 2 shows the position of a pressure sensor 40 for use in the system 10 shown in FIG. 1. Specifically, an output of the pressure sensor 40 can be used for real-time adjustment of alignment and/or docking pressure of the contact element 26 on the cornea 36. The applicator 34 shown in FIG. 2 can be used with all of the different contact elements 26 disclosed herein. A more detailed description of the features shown in FIG. 2 can be found in U.S. patent application Ser. No. 13/423,919, titled "APPARATUS AND METHOD FOR CONTROL OF REFRACTIVE INDEX CHANGES IN A MATERIAL" to Jochen Kandulla.

Figure 3A:
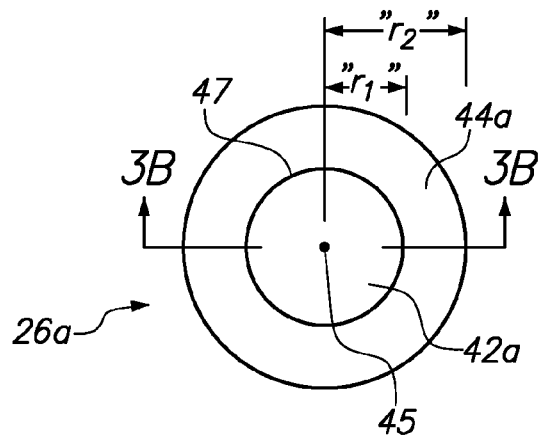
FIG. 3A shows a top view of a hybrid contact element having a circular, disk shaped central portion made of a relatively hard material and an annular shaped peripheral portion made of a relatively soft material.
Figure 3B:
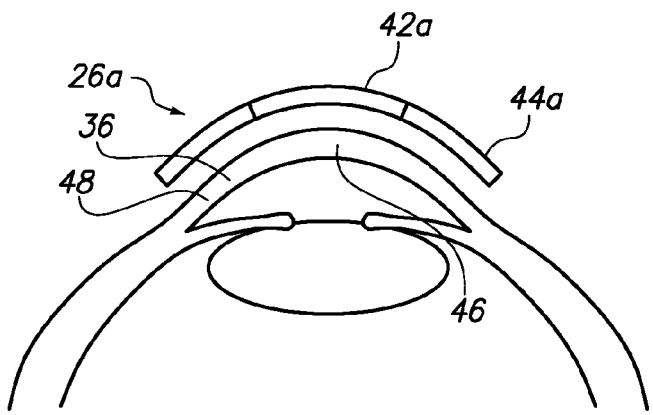
FIG. 3B is a cross-sectional view as seen along line 3B-3B in FIG. 3A showing the contact element of FIG. 3A positioned above and prior to application on a cornea of an eye.
Figure 3C:
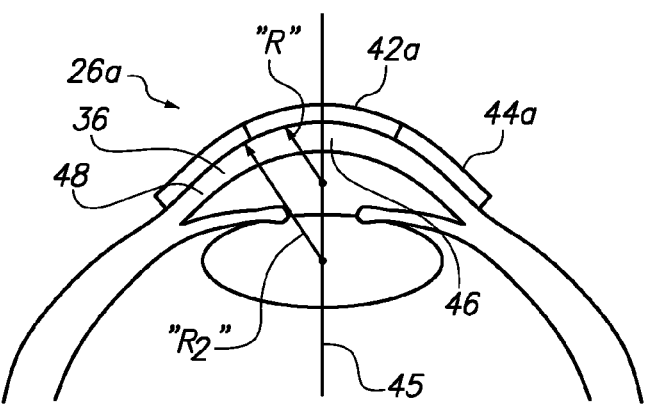
FIG. 3C is a cross-sectional view as in FIG. 3B showing the contact element of FIG. 3A after application on a cornea of an eye.

FIGS. 3A-3C show a first embodiment in which a contact element 26a includes a central portion 42a made of a material that is harder than the cornea 36 (i.e. a first material) and the peripheral portion 44a made of a material that is softer than the cornea 36 (i.e. a second material).

As shown in FIG. 3C, the contact element includes a substantially circular, disk-shaped central portion 42a that defines an axis 45 and a periphery 47. For the central portion 42a, the periphery 47 is positioned in a plane that is perpendicular to the axis 45 and is located at a radial distance "$r_1$" from the axis. Moreover, as shown in FIG. 3C, the central portion 42a is formed with a contact surface having a radius of curvature "$R_1$" when the central portion 42a is in contact with the cornea 36 and is made of a laser transparent material having a hardness "$h_1$".

FIG. 3A shows that the contact element 26a also includes an annular-shaped peripheral portion 44a that extends from the periphery 47 of the central portion 42a to establish the peripheral portion 44a as an extension of the central portion 42a beyond the distance "$r_1$" from the axis. Geometrically, the peripheral portion 44a has an inner radius equal to "$r_1$" and an outer radius of "$r_2$". As shown in FIG. 3C, peripheral portion 44a is formed with a contact surface having a nominal radius of curvature "$R_2$" when the peripheral portion 44a is in contact with the cornea 36, with "$R_1 < R_2$". In addition, the peripheral portion 44a is typically made of a laser transparent material having a hardness "$h_2$", wherein "$h_1 \neq h_2$".

FIG. 3B shows the contact element 26a prior to placement on the cornea 36. As shown, the curvature of the central portion 42a of the contact element 26a can be configured to closely match the curvature of the central region 46 of the cornea 36. On the other hand, the peripheral portion 44a of the contact element 26a can be configured with a curvature slightly larger than the peripheral region 48 of the cornea 36. Comparing FIG. 3B with FIG. 3C, it can be seen that when the contact element 26a is positioned on the cornea 36, little or no deformation of the central portion 42a of the contact element 26a, the central region 46 of the cornea 36 or the peripheral region 48 of the cornea 26a has occurred. On the other hand, the relatively soft peripheral portion 44a of the contact element 26a has slightly deformed to match the curvature of the peripheral region 48 of the cornea 36.

Figure 3D:
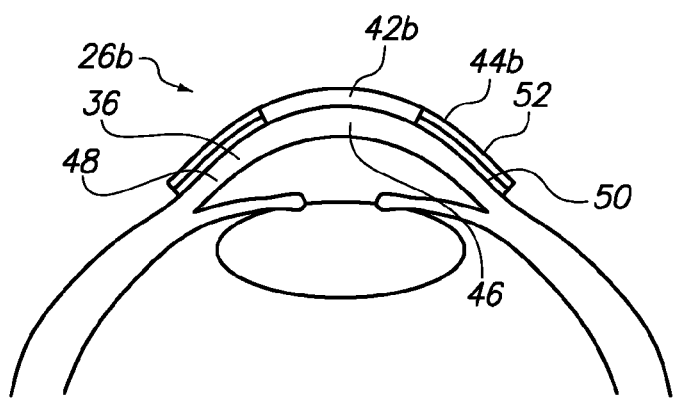
FIG. 3D is a cross-sectional view as in FIG. 3B showing the another embodiment of a contact element having a deformable peripheral portion that is backed by a harder material.

FIG. 3D shows another embodiment of a contact element 26b having a peripheral portion 44b having a deformable portion 50 and a backing portion 52. For the peripheral portion 44b, the deformable portion 50 is made of a relatively soft material for contact with the cornea 36 and the backing portion 52 is made of a relatively hard material (i.e. a material harder than the deformable portion 50). For example, the material used for the backing portion 52 may be the same material used for the central portion 42b (and in some cases may be contiguous with the central portion 42b) or another material. With this arrangement, more of the docking pressure can be applied via the more curved soft material of the deformable portion 50 (rather than central portion 42b).

Figure 4A:
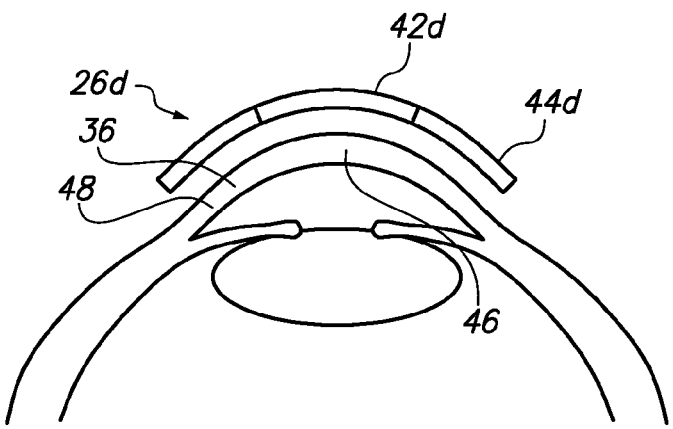
FIG. 4A is a cross-sectional view as in FIG. 3B showing another embodiment of a contact element positioned above and prior to application on a cornea of an eye, the contact element having a circular, disk shaped central portion made of a relatively soft material and an annular shaped peripheral portion made of a relatively hard material.
Figure 4B:
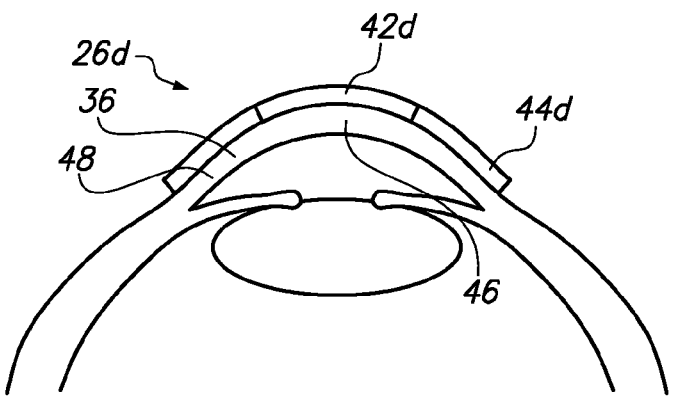
FIG. 4B is a cross-sectional view as in FIG. 3B showing the contact element of FIG. 4A after application on a cornea of an eye.

FIGS. 4A and 4B show another embodiment in which a contact element 26d includes a central portion 42d made of a material that is softer than the cornea 36 and peripheral portion 44d that is made of a material that is harder than the cornea 36. FIG. 4A shows the contact element 26*d* prior to placement on the cornea 36. As shown, before placement on the cornea 36, the curvature of the inner surface of the peripheral portion 44*d* of the contact element 26*d* is configured to closely match the curvature of the peripheral region 48 of the cornea 36. On the other hand, the central portion 42*d* of the contact element 26*d* can have a curvature that slightly differs from the central region 46 of the cornea 36. For example, for the embodiment shown, the central portion 42*d* of the contact element 26*d* can have a curvature that is slightly flatter than the central region 46 of the cornea 36.

Comparing FIG. 4A with FIG. 4B, it can be seen that when the contact element 26*d* is positioned on the cornea 36, little or no deformation of the peripheral portion 44*d* of the contact element 26*d*, the central region 46 of the cornea 36 or the peripheral region 48 of the cornea 36 has occurred. On the other hand, the relatively soft central portion 42*d* of the contact element 26*d* has slightly deformed to match the curvature of the central region 42*d* of the cornea 36. In another embodiment (not shown), the central portion of the contact element can include a deformable portion made of a soft, deformable material for contacting the cornea and a backer portion (see FIG. 3D and corresponding description) made of a harder material supporting the deformable material.

Figure 5A:
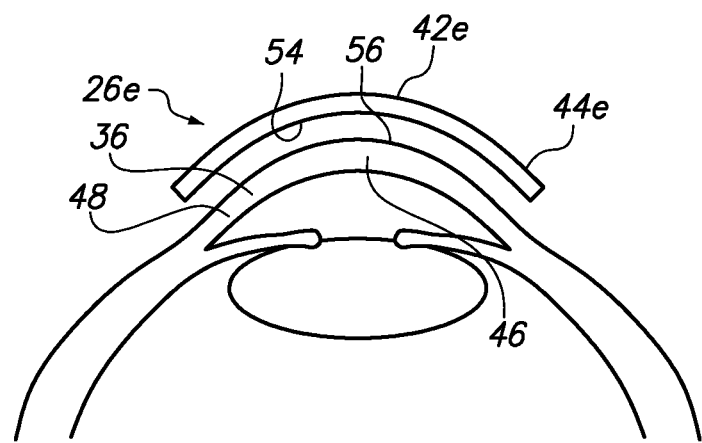
FIG. 5A is a cross-sectional view as in FIG. 3B showing another embodiment of a contact element positioned above and prior to application on a cornea of an eye, the contact element made of a viscoelastic material.
Figure 5B:
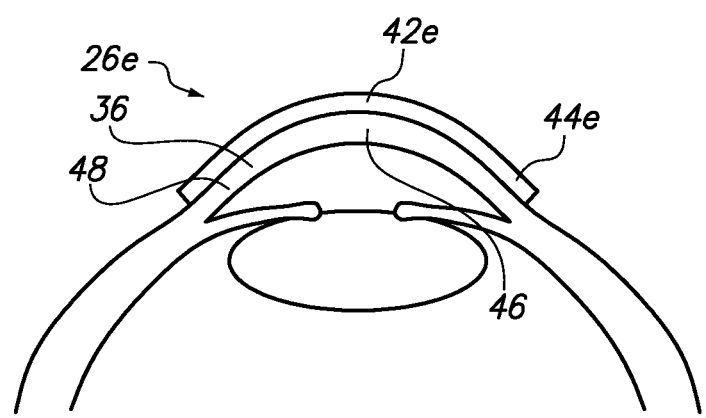
FIG. 5B is a cross-sectional view as in FIG. 3B showing the contact element of FIG. 5A after application on a cornea of an eye.

FIGS. 5A and 5B show another embodiment in which a contact element 26*e* includes a central portion 42*e* and peripheral portion 44*e* with both portions being made of a viscoelastic material. FIG. 5A shows the contact element 26 prior to placement on the cornea 36. As shown, the curvature of the inner contact surface 54 of the contact element 26*e* slightly differs from that of the anterior surface 56 of the cornea 36. Comparing FIG. 5A with FIG. 5B, it can be seen that after the contact element 26*e* has been slowly applied to the cornea 36, the contact element 26*e* molds to the anterior surface 56 of the cornea 36 and little or no deformation of the cornea 36 has occurred. On the other hand, the relatively soft central portion 42*e* of the contact element 26*e* has slightly deformed to match the curvature of the central region 46 of the cornea 36.

Figure 6:
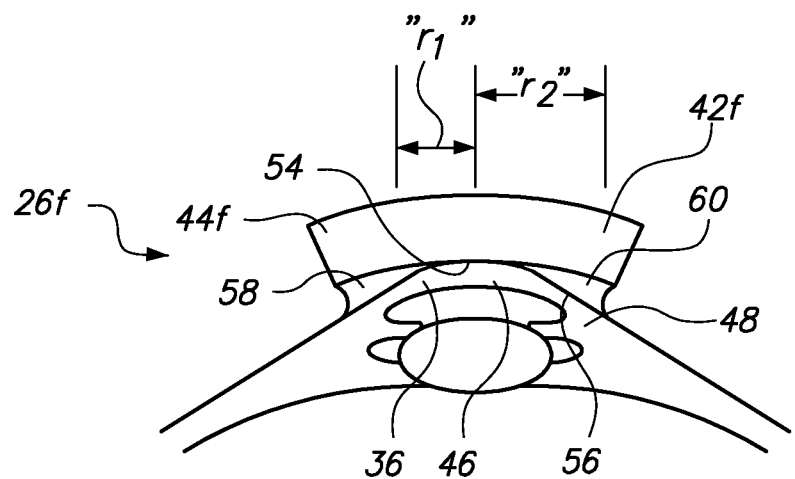
FIG. 6 is a cross-sectional view as in FIG. 3B of another embodiment of a contact element shown positioned on a cornea of an eye, the contact element having a rigid central portion and a liquid peripheral portion.

FIG. 6 shows another embodiment in which a contact element 26*f* includes a central portion 42*f* and peripheral portion 44*f*. In more geometric terms, the contact element 26*f* can include a substantially circular, disk-shaped central portion 42*f* having a radius "$r_1$", and an annular-shaped peripheral portion 44*f* that extends from the central portion 42*f* beyond the distance "$r_1$" to a radius "$r_2$".

Continuing with FIG. 6, when docked, the cornea 36 and contact element 26*f* are in contact over the central region 46*f* of the cornea 36. On the other hand, before the contact element 26*f* is applied, the curvature of the peripheral portion 44*f* of the contact element 26*f* slightly differs from the curvature of the peripheral region 48 of the cornea 36. The result is that a gap 58 is established between the peripheral portion 44*f* of the contact element 26*f* and the peripheral region 48 of the cornea 36. As shown, a liquid 60 can be introduced into the gap 58 to establish a contact element 26*f* which conforms to the anterior surface 56 of the cornea 36 at both the central region 46 of the cornea 36 and the peripheral region 48 of the cornea 36. In some implementations, the central portion 42*f* of the contact element 26*f* can be made of material that is as hard, and typically harder, than the cornea 36. In this case, as shown in FIG. 6, after the central portion 42*f* of the contact element 26*f* has been applied to the cornea 36, the curvature of the inner contact surface 54 closely matches the curvature of the anterior surface 56 of the central region 46 of the cornea 36.

Figure 6A:
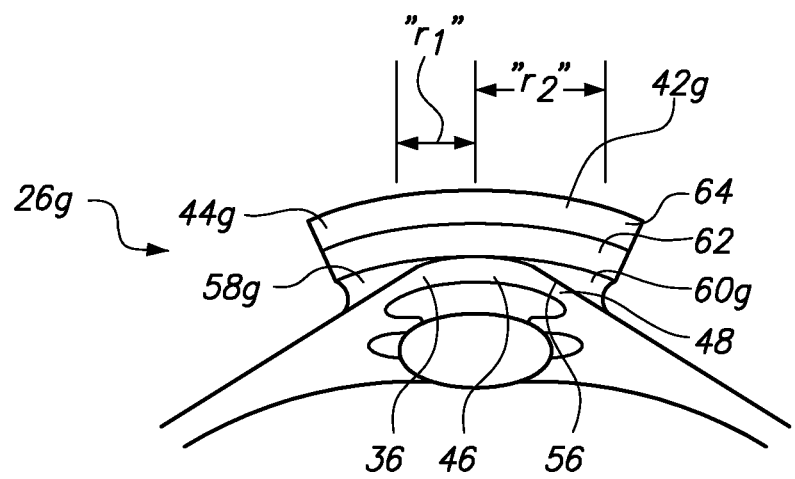
FIG. 6A is a cross-sectional view as in FIG. 3B of another embodiment of a contact element shown positioned on a cornea of an eye, the contact element having a central portion with a soft contact surface and a hard backing and a liquid peripheral portion.

FIG. 6A shows another embodiment in which a contact element 26*g* includes a central portion 42*g* and peripheral portion 44*g*. In more geometric terms, the contact element 26*g* can include a substantially circular, disk-shaped central portion 42*g* having a radius "$r_1$", and an annular-shaped peripheral portion 44*g* that extends from the central portion 42*g* beyond the distance "$r_1$" to a radius "$r_2$".

FIG. 6A also shows that the central portion 42*g* of the contact element 26*g* can have a deformable portion 62 made of a soft, deformable material for contacting the cornea 36 and a backer portion 64 made of a harder material supporting the deformable material. When docked, as shown, the cornea 36 and contact element 26*g* are in contact over the central region 46 of the cornea 36. On the other hand, before the contact element 26*g* is applied, the curvature of the peripheral portion 44*g* of the contact element 26*g* slightly differs from the curvature of the peripheral region 48 of the cornea 36. The result is that a gap 58*g* is established between the peripheral portion 44*g* of the contact element 26*g* and the peripheral region 48 of the cornea 36. As shown, a liquid 60*g* can be introduced into the gap 58*g* to establish a contact element 26*g* which conforms to the anterior surface 56 of the cornea 36 at both the central region 46 of the cornea 36 and the peripheral region 48 of the cornea 36.

Figure 7:
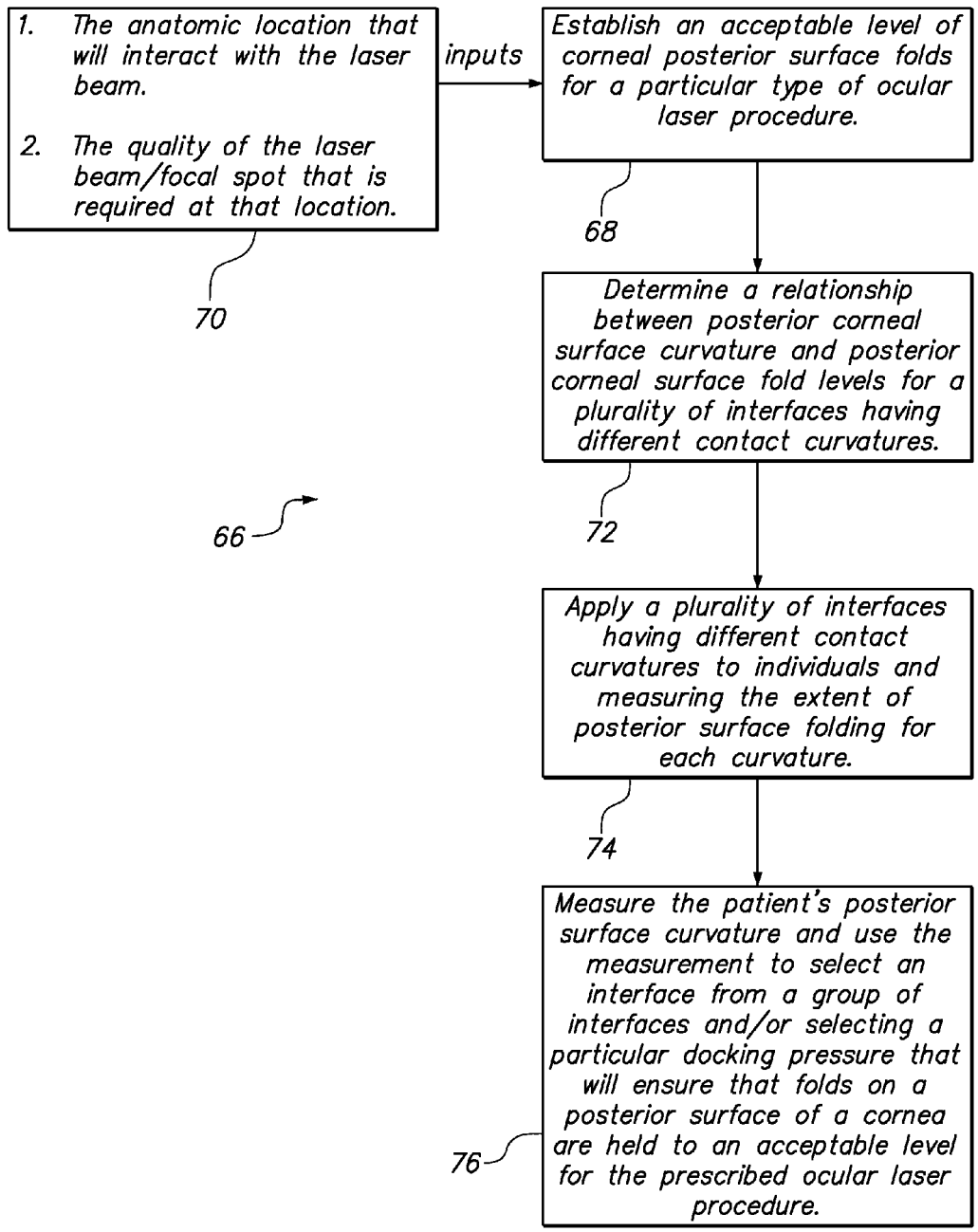
FIG. 7 is a flowchart illustrating a process for determining a contact element curvature for a patient which ensures that folds on a posterior surface of a cornea are held to an acceptable level for a particular laser treatment procedure.

FIG. 7 shows a flowchart illustrating a process 66 for determining a contact element curvature for a patient which ensures that folds on a posterior surface of a cornea are held to an acceptable level. The acceptable level, in turn, can vary from one type of ocular laser procedure to another. This method envisions selecting a contact element for a patient from a group of contact elements having different curvatures.

As shown in FIG. 7, the process 66 can begin by establishing an acceptable level of corneal posterior surface folds for a particular type of ocular laser procedure (Step 68). As shown by Block 70, procedure specific inputs useful in achieving this step can include the anatomic location that will interact with the surgical and/or diagnostic laser beam and the quality of the laser beam/focal spot that is required at that location.

Once an acceptable level of folds on the corneal posterior surface has been established for the particular treatment program, Step 72 of process 66 shows that a relationship between posterior corneal surface curvature and posterior corneal surface fold levels for a plurality of interfaces having different contact curvatures can be determined. For example, the posterior surface curvature for a group of individuals can be measured and evaluated in Step 72 of process 66. The amount of folds that are generated may depend on the change in posterior surface curvature between the pre-docking and docked corneal configurations. To make a prediction whether the level of folds is acceptable may in some cases include measuring the posterior corneal curvature twice: prior to docking and after docking. Then, Step 74 of process 66 indicates that a plurality of interfaces having different contact curvatures can be applied to each individual and the extent of posterior surface folding can be measured for each curvature. With this data, the patient's posterior surface curvature is measured in Step 76 of process 66 and used to select an interface from a group of interfaces and/or used to select a particular docking pressure that will ensure that folds on a posterior surface of a cornea are held to an acceptable level for the prescribed ocular laser procedure. For example, the process 66 may be particularly applicable when using the embodiments described above in which a softer peripheral portion that is intentionally steeper in its pre-docked configuration than the corresponding peripheral corneal region, in order to apply much of the docking pressure at the peripheral portion rather than the central portion of the contract element. Alternatively, another indicator other than posterior curvature may be used to determine the most appropriate combination of patient interface and docking pressure.

While the particular Adaptable Patient Interface as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A patient interface for stabilizing an eye of a patient during an ophthalmic laser procedure which comprises:
    a substantially circular, disk-shaped central portion defining an axis and a periphery, wherein the periphery is in a plane perpendicular to the axis and is located at a radial distance "$r_1$" from the axis, and further wherein the central portion is formed with a contact surface having a nominal radius of curvature "$R_1$" when the central portion is in contact with the eye, and is made of a transparent material having a hardness "$h_1$"; and
    an annular-shaped peripheral portion having an inner radius equal to "$r_1$" and an outer radius of "$r_2$", wherein the peripheral portion extends from the periphery of the central portion to establish the peripheral portion as an extension of the central portion beyond the distance "$r_1$" from the axis, wherein the peripheral portion is formed with a contact surface having a nominal radius of curvature "$R_2$" when the peripheral portion is in contact with the eye, and wherein the peripheral portion is made of a transparent material having a hardness "$h_2$", wherein "$h_1 \neq h_2$" and "$R_1 < R_2$".

2. A patient interface as recited in claim 1 wherein the peripheral portion is a solid material.

3. A patient interface as recited in claim 1 wherein "$h_1 > h_2$".

4. A patient interface as recited in claim 1 wherein "$h_1 < h_2$".

5. A patient interface as recited in claim 1 wherein said central portion has a curvature between 35-45 diopters.

6. A patient interface as recited in claim 1 wherein said peripheral portion is a liquid crystal material.

7. A patient interface as recited in claim 1 wherein said central and peripheral portions are contiguous.

8. A patient interface as recited in claim 1 wherein said central portion substantially stabilizes the eye to reduce the effects of heartbeat induced ocular movements to a level suitable for a selected laser procedure.

9. A patient interface as recited in claim 1 further comprising an imaging system for real-time adjustment of alignment and docking pressure between said patient interface and said eye.

10. A patient interface for stabilizing an eye of a patient during an ophthalmic laser procedure which comprises:
    a substantially circular, disk-shaped central portion defining an axis and a periphery, wherein the periphery is in a plane perpendicular to the axis and is located at a radial distance "$r_1$" from the axis, and further wherein the central portion is formed with a contact surface having a radius of curvature "$R_1$" when the central portion is in contact with the eye, and is made of a transparent material; and
    an annular-shaped peripheral portion having an inner radius less than "$r_1$", wherein the peripheral portion is an extension of the central portion, is a liquid, and is held between the central portion and the eye by capillary forces, and wherein the peripheral portion is established having a radius of curvature "$R_2$", with "$R_1 < R_2$".

11. A patient interface as recited in claim 10 wherein the peripheral portion has an outer radius substantially equal to "$r_1$".

12. A patient interface as recited in claim 10 wherein said peripheral portion is a liquid gel.

13. A patient interface as recited in claim 10 wherein said central portion has a curvature between 35-45 diopters.

14. A patient interface as recited in claim 10 wherein said central portion substantially stabilizes the eye to reduce the effects of heartbeat induced ocular movements to a level suitable for a selected laser procedure.

15. A patient interface as recited in claim 10 further comprising an imaging system for real-time adjustment of alignment and docking pressure between said patient interface and said eye.

* * * * *